(12) United States Patent
Kato

(10) Patent No.: US 10,525,243 B2
(45) Date of Patent: Jan. 7, 2020

(54) MICRONEEDLE UNIT AND MICRONEEDLE ASSEMBLY

(71) Applicant: TOPPAN PRINTING CO., LTD., Taito-ku (JP)

(72) Inventor: Hiroyuki Kato, Taito-ku (JP)

(73) Assignee: TOPPAN PRINTING CO., LTD., Taito-ku (JP)

(*) Notice: Subject to any disclaimer, the term of this patent is extended or adjusted under 35 U.S.C. 154(b) by 149 days.

(21) Appl. No.: 15/217,306

(22) Filed: Jul. 22, 2016

(65) Prior Publication Data

US 2016/0325081 A1    Nov. 10, 2016

Related U.S. Application Data

(63) Continuation of application No. PCT/JP2015/051733, filed on Jan. 22, 2015.

(30) Foreign Application Priority Data

Jan. 24, 2014  (JP) ................................. 2014-011524

(51) Int. Cl.
*A61M 37/00*    (2006.01)

(52) U.S. Cl.
CPC . *A61M 37/0015* (2013.01); *A61M 2037/0023* (2013.01); *A61M 2037/0046* (2013.01)

(58) Field of Classification Search
CPC .. A61M 2037/0023; A61M 2037/0046; A61M 37/0015
See application file for complete search history.

(56) References Cited

U.S. PATENT DOCUMENTS

2008/0114298 A1*  5/2008  Cantor ............. A61M 37/0015
                                                 604/117
2008/0183144 A1*  7/2008  Trautman .......... A61M 37/0015
                                                 604/272
(Continued)

FOREIGN PATENT DOCUMENTS

JP    2010-516337 A    5/2010
JP    2012-183358 A    9/2012
(Continued)

OTHER PUBLICATIONS

Extended European Search Report dated Aug. 16, 2017 in Patent Application No. 15740027.6.

(Continued)

*Primary Examiner* — Quynh-Nhu H. Vu
(74) *Attorney, Agent, or Firm* — Oblon, McClelland, Maier & Neustadt, L.L.P.

(57) ABSTRACT

A microneedle unit includes a microneedle including a facing surface having at least one projection and a support surface opposite to the facing surface, a recessed container having a housing space between an opening and a bottom of the recessed container for housing the microneedle such that the microneedle has the facing surface facing outside of the recessed container through the opening, and an adhering structure having a first contact surface adhered to the bottom of the recessed container and a second contact surface adhered to the support surface of the microneedle. The recessed container is deformable such that the bottom is displaced in the pressing direction, that the at least one projection is displaced in the pressing direction on an outside of the housing space, and that a portion of the second contact surface positioned outside the support surface is pushed toward the outside of the housing space.

20 Claims, 8 Drawing Sheets

(56) References Cited

U.S. PATENT DOCUMENTS

| | | | |
|---|---|---|---|
| 2008/0195035 A1* | 8/2008 | Frederickson | A61K 9/0021 |
| | | | 604/22 |
| 2012/0029434 A1* | 2/2012 | Kobayashi | A61M 37/0015 |
| | | | 604/173 |
| 2012/0184916 A1* | 7/2012 | Kobayashi | A61M 37/0015 |
| | | | 604/180 |
| 2013/0006219 A1 | 1/2013 | Cantor et al. | |
| 2013/0023749 A1 | 1/2013 | Afanasewicz et al. | |
| 2016/0121092 A1* | 5/2016 | Kato | A61M 37/0015 |
| | | | 604/173 |

FOREIGN PATENT DOCUMENTS

| | | | |
|---|---|---|---|
| JP | 2013-226427 A | 11/2013 | |
| WO | WO 2008/020632 A | 2/2008 | |
| WO | WO 2009/107806 A2 | 9/2009 | |
| WO | WO 2010/095456 A1 | 8/2010 | |

OTHER PUBLICATIONS

International Search Report dated Apr. 7, 2015 in PCT/JP2015/051733, filed Jan. 22, 2015.
Combined Chinese Office Action and Search Report dated Sep. 4, 2018 in Patent Application No. 201580004687.9, 16 pages. (with English language translation and English language translation of categories of cited documents).

* cited by examiner

MICRONEEDLE UNIT AND MICRONEEDLE ASSEMBLY

CROSS-REFERENCE TO RELATED APPLICATIONS

The present application is a continuation of International Application No. PCT/JP2015/051733, filed Jan. 22, 2015, which is based upon and claims the benefits of priority to Japanese Application No. 2014-011524, filed Jan. 24, 2014. The entire contents of these applications are incorporated herein by reference.

BACKGROUND OF THE INVENTION

Field of the Invention

The technique of the present disclosure relates to microneedle units having a microneedle and microneedle assemblies having the microneedle unit and an applicator used for piercing the microneedle into a puncture target.

Discussion of the Background

Percutaneous absorption methods include administration of substances such as drugs into a puncture target such as a human in a painless manner so as to deliver substances into the body through the skin.

Percutaneous absorption methods include piercing the microneedle into the skin, for example, as described in PTL 1. The microneedle includes a projection configured to penetrate the stratum corneum, and the projection has a size that does not provoke pain to the puncture target. The drug is absorbed into the skin through a hole created in the skin by the projection.

PTL 1: WO 2008/020632 A

SUMMARY OF THE INVENTION

According to one aspect of the present invention, a microneedle unit includes a microneedle including a facing surface having at least one projection formed thereon and a support surface opposite to the facing surface, a recessed container having a housing space between an opening and a bottom of the recessed container for housing the microneedle such that the microneedle has the facing surface facing outside of the recessed container through the opening, and an adhering structure having a first contact surface adhered to the bottom of the recessed container and a second contact surface adhered to the support surface of the microneedle, the second contact surface extending outside the support surface. Upon receiving an external force applied to the bottom in a pressing direction from the bottom to the opening, the recessed container is deformable in a first manner such that the bottom is displaced in the pressing direction, that the at least one projection is displaced in the pressing direction on an outside of the housing space, and that a portion of the second contact surface positioned outside the support surface is pushed toward the outside of the housing space.

According to another aspect of the present invention, a microneedle assembly includes a microneedle unit, and an applicator of the microneedle unit. The microneedle unit includes a microneedle which includes a facing surface having at least one projection formed thereon and a support surface opposite to the facing surface, a recessed container having a housing space between an opening and a bottom of the recessed container for housing the microneedle such that the microneedle has the facing surface facing outside of the recessed container through the opening, the recessed container further including a flange portion that extends outward from an edge of the opening, and an adhering structure having a first contact surface adhered to the bottom of the recessed container and a second contact surface adhered to the support surface of the microneedle, the second contact surface extending outside the support surface. Upon receiving an external force applied to the bottom in a pressing direction from the bottom to the opening of the recessed container, the recessed container is deformable in a first manner such that the bottom is displaced in the pressing direction, that the at least one projection is displaced in the pressing direction on an outside of the housing space, and that a portion of the second contact surface positioned outside the support surface is pushed toward the outside of the housing space, and the applicator has a surface that makes contact with the flange portion of the microneedle unit when the flange portion is pushed against the puncture target.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
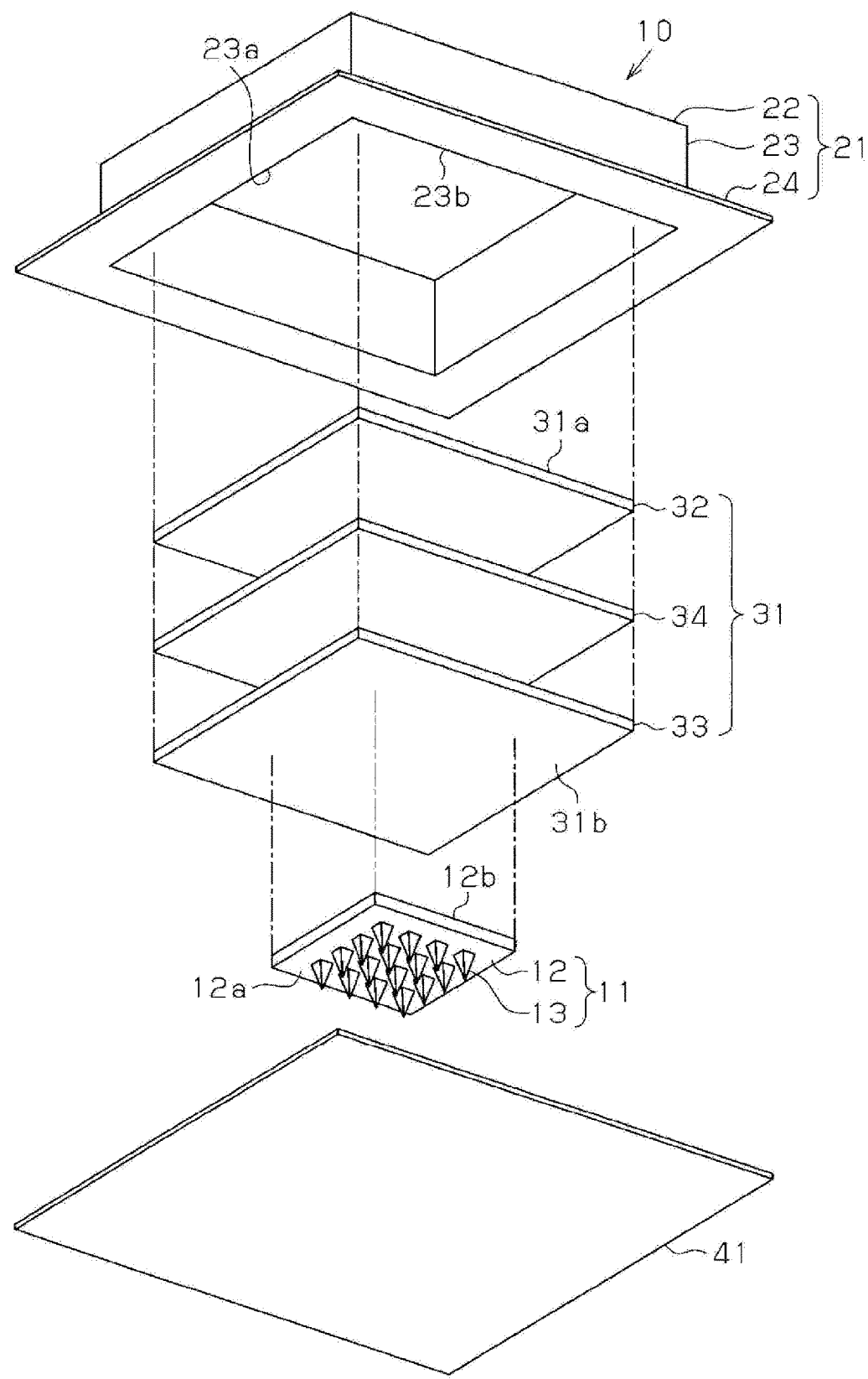
FIG. 1 is an exploded perspective view which shows an exploded perspective configuration of components of a microneedle in a first embodiment of a microneedle unit of the present disclosure.

The embodiments will now be described with reference to the accompanying drawings, wherein like reference numerals designate corresponding or identical elements throughout the various drawings.

First Embodiment

With reference to FIGS. 1 to 8, a first embodiment of a microneedle unit according to the technique of the present disclosure will be described. The following describes an overall configuration of a microneedle unit, a configuration of a microneedle, a constituent material of the microneedle unit and an operation of the microneedle unit.

Overall Configuration of Microneedle Unit

With reference to FIG. 1, an overall configuration of a microneedle unit will be described. FIG. 1 shows one example of the overall configuration of the microneedle unit.

As shown in FIG. 1, a microneedle unit 10 includes a microneedle 11, a container 21 that houses the microneedle 11, and an adhering section 31 that adheres the container 21 and the microneedle 11.

The microneedle 11 includes a base body 12, and the base body 12 includes a facing surface 12a. The facing surface 12a is provided with one or more projections 13. An object which is pierced by the microneedle 11 is referred to as a puncture target. When the microneedle unit 10 is used, the facing surface 12a faces the puncture target. The base body 12 includes a support surface 12b which is a surface opposite to the facing surface 12a.

The container 21 is a recessed container which includes a bottom 22 that supports the support surface of the base body 12 and an opening 23b. The container 21 has a housing space 23a which is a recess that houses the microneedle 11. The housing space 23a is connected to the opening 23b. A direction from the bottom 22 to the opening 23b is referred to as a pressing direction. When the facing surface 12a and the puncture target face each other and an external force in the pressing direction is applied to the bottom 22, the container 21 exhibits a first deformation. The first deformation of the container 21 includes displacement of the bottom 22 in the pressing direction and displacement of the projections 13 in the pressing direction on the outside of the housing space 23a.

The adhering section 31 has adhesiveness so as to adhere to the bottom 22 of the container 21 and the support surface 12b of the base body 12 of the microneedle 11. The adhering section 31 includes a container contact surface 31a that is in contact with the bottom 22 of the container 21. The adhering section 31 further includes a target contact surface 31b that is in contact with the support surface 12b and extends from the support surface 12b to an area surrounding the support surface 12b. When the first deformation occurs to the container 21 and the projections 13 are pierced into the puncture target, a portion of the puncture target located in an area surrounding the facing surface 12a comes into contact with the target contact surface 31b. The container contact surface 31a is one example of the first contact surface, and the target contact surface 31b is one example of the second contact surface.

When a portion of the target contact surface 31b located in an area surrounding the support surface 12b is adhered to the puncture target and then the bottom 22 receives a force in a direction opposite to the pressing direction, that is, when the bottom 22 receives a force in the direction separating from the puncture target, the container 21 exhibits a second deformation. The second deformation of the container 21 includes displacement of the bottom 22 in the direction opposite to the pressing direction. When the second deformation occurs in the container 21, the target contact surface 31b maintains adhesion to the puncture target while the container contact surface 31a is peeled from the bottom 22 of the container 21.

The base body 12 of the microneedle 11 may have a polygonal plate shape such as a rectangular plate shape or may have a disk shape. The facing surface 12a of the base body 12 only needs to have an area not smaller than an area that can be provided with at least one projection 13. The facing surface 12a of the base body 12 may have a flat surface, a curved surface or both flat and curved surfaces. The support surface 12b of the base body 12 may have a curved surface or may have both a flat surface and a curved surface.

When one projection 13 is provided on the facing surface 12a, the projection 13 may be disposed at the center of the facing surface 12a or may be disposed at any position other than the center.

When a plurality of projections 13 are provided on the facing surface 12a, the plurality of projections 13 may be arranged in a regular or irregular manner. If the plurality of projections 13 are regularly arranged, the plurality of projections 13 may be arranged, for example, in a grid pattern, a close-packed pattern or a concentric pattern.

Each projection 13 may have any shape as long as it can puncture the puncture target and may be, for example, a pyramid shape, frustum, column or blade shape which extends in one direction, which is an extending direction. When the projection 13 has a pyramid shape, the projection 13 may have a conical shape or a polygonal pyramid shape. When the projection 13 has a frustum shape, the projection 13 may have a conical frustum shape or a polygonal frustum shape. When the projection 13 has a columnar shape, the columnar shape may be a round columnar shape or a polygonal columnar shape.

The projections 13 may have two or more different shapes in the extending direction, for example, two or more of the above-mentioned pyramid shape, frustum shape and columnar shape. The outer peripheral surface of the projections 13 may have a twist or a step. For the purpose of facilitating puncturing the projections 13 into a puncture target, it is preferable that at least a tip of the projection 13 has a pyramid shape.

When the microneedle 11 includes the plurality of projections 13, each of the plurality of projections 13 may have the same or different shapes. For the purpose of facilitating manufacturing of the plurality of projections 13, it is preferable that the plurality of projections 13 have the same shape.

When the microneedle 11 includes the plurality of projections 13, each of the plurality of projections 13 may extend in the same direction or in the direction crossing each other. When each of the plurality of projections 13 extends in the direction crossing each other, the tips of the adjacent projections 13 are not in contact with each other.

When the microneedle 11 includes the plurality of projections 13, each of the plurality of projection 13 may have the same or different length in the extending direction.

The container 21, which is a recessed container, may have a cylindrical shape, hemispherical shape or semielliptical shape. When the container 21 has a cylindrical shape, the container 21 includes a cylindrical body 23 having two cylindrical ends and a bottom 22 that closes one of the cylindrical ends. When the container 21 has a hemispherical shape or a semielliptical shape, the container 21 has a curved bottom. When the container 21 has a cylindrical shape, the container 21 may be a round cylindrical shape or a polygonal cylindrical shape such as a rectangular cylindrical shape. When the container 21 has a cylindrical shape, the bottom 22 may have a flat plate shape, a curved plate shape that is recessed toward the opening 23b or a curved plate shape that bulges in a direction away from the opening 23b. In the bottom 22 of the container 21, the area that is in contact with the base body 12 is larger than the area of support surface 12b of the base body 12.

When the container 21 has a cylindrical shape, the microneedle 11 may be disposed at the center or a position other than the center of the bottom 22. It is preferable that the length of the container 21 in the extending direction is larger than the length of the microneedle 11 in the extending direction.

The container 21 deforms when a force in the direction from the bottom 22 to the opening 23b is applied to the bottom 22. The deformation of the container 21 may be plastic deformation or elastic deformation. In plastic deformation of the container 21, the container 21 remains in the same shape when the force is released from the bottom 22. In elastic deformation of the container 21, the container 21 returns to the original shape when the force is released from the bottom 22.

The container 21 may include a flange section 24, which extends from the edge of the opening 23b to the outside of the housing space 23a. The flange section 24 may be disposed on part of the edge of the opening 23b or on the entire edge of the opening 23b.

The adhering section 31 has, for example, a plate shape.

The container contact surface 31a of the adhering section 31 has adhesive strength to the bottom 22 of the container 21, which is referred to as a bottom adhesive strength. Further, a portion of the target contact surface 31b located in the area surrounding the support surface 12b has adhesive strength to the puncture target, which is referred to as target adhesive strength.

When the projections 13 of the microneedle 11 are pierced into the puncture target, the bottom adhesive strength and the target adhesive strength may be the same. In this case, for example, a surface roughness of the bottom 22 of the container 21 is smaller than a surface roughness of the puncture target. Accordingly, when a portion of the target contact surface 31b located in the area surrounding the support surface 12b is adhered to the puncture target and then the bottom 22 is separated from the puncture target, the container contact surface 31a is peeled from the container 21. Alternatively, the target contact surface 31b is formed as one continuous surface, while the container contact surface 31a is made up of a plurality of pieces. This also allows the container 21 to be peeled from the microneedle 11, since a force is applied to the respective pieces of the container contact surface 31a to peel the pieces from the bottom 22 when the bottom 22 is separated from the puncture target.

Alternatively, in the adhering section 31, the bottom adhesive strength may be smaller than the target adhesive strength when the projections 13 of the microneedle 11 are pierced into the puncture target. In the adhering section 31, the difference between the bottom adhesive strength and the target adhesive strength may be caused by the difference between the surface shape of the bottom 22 and the surface shape of the puncture target or by the difference between the forming material of the container contact surface 31a and the forming material of the target contact surface 31b. Further, the difference between the bottom adhesive strength and the target adhesive strength may be caused by the difference between the area of the container contact surface 31a which is in contact with the bottom 22 and the area of the target contact surface 31b which is in contact with the puncture target, or combinations thereof.

The adhering section 31 may be formed of a single layer or a plurality of layers laminated in the extending direction. When the adhering section 31 is formed of a single layer, the composition of the adhering section 31 may be uniform in the extending direction or may vary in the extending direction.

When the adhering section 31 is made up of a plurality of different layers laminated in the extending direction, the adhering section 31 serves as a laminate that adheres the bottom 22 of the container 21 to the support surface 12b of the base body 12. When the adhering section 31 is made up of a plurality of layers, the adhering section 31 includes, for example, a container contact section 32 having the container contact surface 31a that is in contact with the bottom 22 of the container 21 and the target contact section 33 having the target contact surface 31b of the support surface 12b and the target. The container contact section 32 and the target contact section 33 each have a layer shape. In the adhering section 31 having the container contact section 32 and the target contact section 33, the container contact section 32 is one example of the first portion and the target contact section 33 is one example of the second portion.

The target contact section 33 extends from the support surface 12b of the base body 12 to the area surrounding the support surface 12b. When the projections 13 pierce the puncture target, a portion of the puncture target located in the area surrounding the facing surface 12a comes into contact with the target contact surface 31b of the target contact section 33. It is preferable that the forming material of the container contact section 32 and the forming material of the target contact section 33 are different from each other. The target contact section 33 has adhesiveness on the target contact surface 31b so as to exhibit the adhesive strength to the puncture target.

When the adhering section 31 includes the container contact section 32 and the target contact section 33, the adhering section 31 includes a portion located on the container contact surface 31a and exhibiting the adhesive strength to the bottom 22 of the container 21 and a portion located on the target contact surface 31b and exhibiting the adhesive strength between the adhering section 31 and the puncture target, which are independent of each other. Accordingly, compared with the adhering section 31 formed as a single layer, the degree of freedom of the forming material of the adhering section 31 is improved.

When the adhering section 31 is made up of a plurality of layers, the adhering section 31 preferably includes a support section 34 between the container contact section 32 and the target contact section 33 in the direction in which the microneedle 11 faces the puncture target, that is, in the direction parallel with the extending direction. The support section 34 is formed in a layer shape and has rigidity higher than that of the target contact section 33. The support section 34 is one example of the third portion.

According to the configuration in which the support section 34 is disposed between the container contact section 32 and the base body 12, the support section 34 having high rigidity can prevent deformation of the target contact section 33 when the container 21 and the target contact section 33 are separated from each other and the container 21 is peeled from the microneedle 11. Accordingly, the base body 12 and thus the projections 13 are prevented from being easily deformed. As a result, when the container 21 is peeled from the microneedle 11, the projections 13 of the microneedle 11 pierced into the puncture target are prevented from being easily dropped off from the puncture target.

The adhering section 31 may have a polygonal plate shape or a disc shape. In the adhering section 31, the area of the container contact surface 31a and the area of the target contact surface 31b which comes into contact with the puncture target may be different in the state that the projections 13 are pierced into the puncture target. For the purpose of decreasing the adhesive strength of the container contact surface 31a to the container 21 to be smaller than the adhesive strength of a portion of the target contact surface 31b which is in contact with the puncture target, it is preferable that the area of the container contact surface 31a is smaller than the area of the target contact surface 31b.

In the adhering section 31, the outer edge of the container contact surface 31a may be positioned inside the outer edge of the support surface 12b of the microneedle 11. In the adhering section 31, part of the outer edge of the container contact surface 31a may be positioned outside the outer edge of the support surface 12b, or the entire outer edge of the container contact surface 31a may be positioned outside the outer edge of the support surface 12b. In order to reduce variation of the adhesive strength of the adhering section 31 in the circumferential direction of the microneedle 11, it is preferable that the entire outer edge of the container contact surface 31a is positioned outside the outer edge of the support surface 12b.

In the adhering section 31, a distance between the outer edge of the target contact surface 31b and the outer edge of the support surface 12b of the microneedle 11 may be constant on the entire outer edge of the target contact surface 31b or may be different between one part of the outer edge and the other part of the outer edge. In order to reduce variation of the adhesive strength of the adhering section 31 in the circumferential direction of the microneedle 11, it is preferable that the distance between the outer edge of the target contact surface 31b and the outer edge of the support surface 12b of the microneedle 11 is constant on the entire outer edge of the target contact surface 31b.

When the adhering section 31 is made up of a plurality of layers, each of the plurality of layers may have the same shape and size as those of the other layers, and preferably, the plurality of layers entirely overlap each other. In the adhering section 31, the container contact section 32, the target contact section 33 and the support section 34 may each include a portion that does not overlap the other layers in the extending direction as long as the container contact section 32, the target contact section 33 and the support section 34 do not interfere with functions of the other layers.

The microneedle unit 10 may include a sealing section 41 that closes at least part of the opening 23b. The sealing section 41 may have a plate shape, cylindrical shape, hemispherical shape or semielliptical shape. When the sealing section 41 has a cylindrical shape, the cylindrical shape having two cylindrical ends includes a bottom that closes one of two cylindrical ends. When the length of the housing space 23a in the extending direction is smaller than the length of the projection 13 in the extending direction, or alternatively, when the length of the housing space 23a in the extending direction is so small that part of the projection 13 projects from the opening 23 the sealing section 41 may have a cylindrical shape, hemispherical shape or semielliptical shape so as to cover the projection 13 projecting from the opening 23b. When the sealing section 41 has a plate shape, the area of the sealing section 41 is preferably larger than the area of the container 21 surrounded by the edge of the opening 23b.

When the container 21 has one of a cylindrical shape, hemispherical shape and semielliptical shape and the sealing section 41 has one of a cylindrical shape, hemispherical shape and semielliptical shape, the shape and size of the opening 23b of the container 21 are preferably the same as the shape and size of the opening of the sealing section 41. For the purpose of enhancing the reliability of sealing of the container 21 and facilitating manufacturing of the sealing section 41, it is preferable that the sealing section 41 has a plate shape.

The container 21 and the sealing section 41 may be adhered to each other by using an adhesive, or may be connected by heat seal adhesion. Alternatively, the container 21 and the sealing section 41 may have fitting sections which fit to each other. The fitting sections fit to each other to seal the space formed by the container 21 and the sealing section 41.

Configuration of Microneedle

Figure 2:
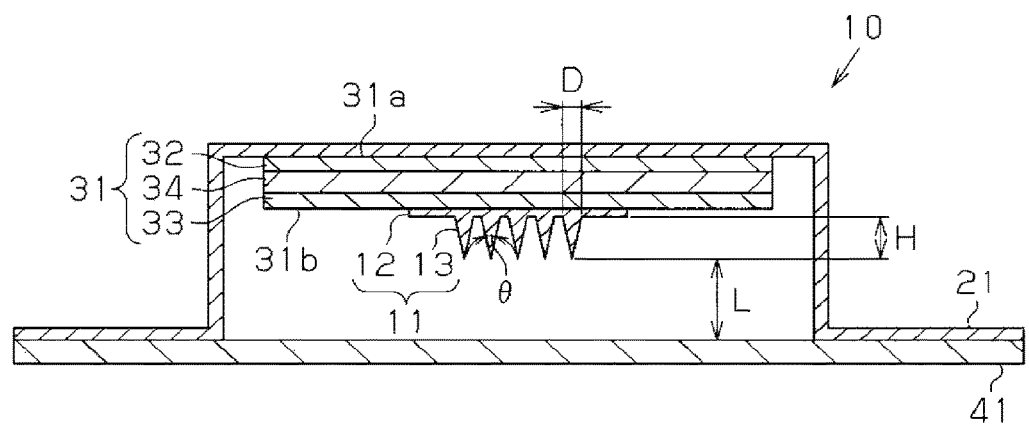
FIG. 2 is a cross sectional view which shows a cross sectional configuration of the microneedle unit in the first embodiment.

With reference to FIG. 2, a configuration of the microneedle 11 will be described. FIG. 2 is a view of a cross sectional configuration of the microneedle unit 10 taken along the plane which is perpendicular to the facing surface 12a and passes through the container 21, the microneedle 11 and the adhering section 31.

As shown in FIG. 2, in the projection 13 of the microneedle 11, a height H of the projection 13 is a length in the extending direction from the facing surface 12a of the base body 12 to the tip which is a distal end of the projection 13. The projection 13 preferably has a height H suitable for creating a hole in the skin, which is the puncture target, and the height H of the projection 13 is preferably in the range from 10 µm to 1000 µm, inclusive.

The height H of the projection 13 is preferably designed depending on where in the skin that the bottom of the hole to be formed in the puncture target is located. When the bottom of the hole is designed to be located in the stratum corneum, the height H of the projection 13 is preferably in the range from 10 µm to 300 µm, inclusive, more preferably in the range from 30 µm to 200 µm, inclusive.

When the bottom of the hole is designed to pass through the stratum corneum of the skin and to be located at a position not reaching the nerve plexus, the height H of the projection 13 is preferably in the range from 200 µm to 700 µm, inclusive, more preferably in the range from 200 µm to 500 µm, inclusive. When the bottom of the hole is designed to pass through the stratum corneum of the skin and to be located at a position not reaching the nerve plexus, the height H of the projection 13 is further preferably in the range from 200 µm to 300 µm, inclusive.

When the bottom of the hole is designed to be located at a position reaching the dermis, the height H of the projection 13 is preferably in the range from 200 µm to 500 µm, inclusive. When the bottom of the hole is designed to be located at a position reaching the epidermis, the height H of the projection 13 is preferably in the range from 200 µm to 300 µm, inclusive.

In the projection 13, the maximum length in the direction perpendicular to the extending direction is a width D, and the width D of the projection 13 is preferably in the range from 1 µm to 300 µm, inclusive. For example, when the projection 13 has a regular quadrangular pyramid shape or a square column shape, the proximal end which is different from the distal end of the projection 13 defines a square shape in the facing surface 12a. The length of the diagonal line of the square area defined by the proximal end of the projection 13 is the width D of the projection 13. Further, for example, when the projection 13 has a conical shape or a columnar shape, the proximal end of the projection 13 defines a circular area in the facing surface 12a. The diameter of the circular shape defined by the proximal end of the projection 13 is the width D of the projection 13.

In the projection 13, an aspect ratio A is the ratio of the height H to the width D (A=H/D). The aspect ratio of the projection 13 is preferably in the range from 1 to 10, inclusive.

When the projection 13 has a pyramid shape at least on the distal end, the angle of the distal end of the projection 13 is a distal end angle θ. The distal end angle θ is a maximum angle of the projection 13 in the cross section taken along the plane perpendicular to the facing surface 12a of the base body 12. For example, when the projection 13 has a regular quadrangular pyramid shape, the distal end angle θ of the projection 13 is an apex angle of an isosceles triangle having the proximal end of the projection 13 as a base and the distal end of the projection 13 as an apex.

When the projection 13 has a pyramid shape at least on the distal end and the bottom of the hole is designed to be located at a position that passes through the stratum corneum, the distal end angle θ is preferably in the range from 5 degrees to 30 degrees, inclusive, more preferably in the range from 10 degrees to 20 degrees, inclusive.

In the microneedle unit 10 having a sealing section 41, a distance between the distal end of the projection 13 and a portion of the sealing section 41 which faces the distal end of the projection 13 is a spaced distance L. The spaced distance L is preferably in the range from 0.1 mm to 10 mm, inclusive. In the configuration having the spaced distance L of not smaller than 0.1 mm, the distal end of the projection 13 can be prevented from coming into contact with the sealing section 41 during shipping of the microneedle unit 10, thereby preventing deformation or damage of the distal end of the projection 13. Further, in the configuration having the spaced distance L of not larger than 10 mm, a space necessary for shipping and storage of the microneedle unit 10 can be prevented from increasing in size during shipping and storage of the microneedle unit 10.

Constituent Material of Microneedle Unit

The forming material of the microneedle 11 is preferably a biocompatible material, that is, a material which functions as the microneedle 11 but does not adversely affect the puncture target to which the microneedle 11 is applied. When the forming material of the microneedle 11 is a biocompatible material, the forming material of the microneedle 11 is silicon, metal, resin or the like. When the forming material of the microneedle 11 is a metal, the forming material is stainless steel, titanium, mangan or the like. When the forming material of the microneedle 11 is a resin, the forming material is medical grade silicone, polylactic acid, polyglycolic acid, polycarbonate cyclic olefin copolymer or the like.

The forming material of the microneedle 11 may be a material having biocompatibility, and soluble in liquid administered to the puncture target by the microneedle unit 10 or liquid administered to the puncture target from outside. When the forming material is a material soluble in liquid, the forming material is, for example, a water soluble polymer.

The water soluble polymer is, for example, alginates, curdlan, chitin, chitosan, glucomannan, polymalic acid, collagen, collagen peptide, hydroxypropyl cellulose, hydroxypropylmethyl cellulose, carboxymethyl cellulose, gelatin, chitosan succinamide, trimethyl chitosan, oligo chitosan, oligo chitin, ethylene glycol chitosan, ethylene glycol chitin and the like.

In the microneedle 11, the forming material of the base body 12 and the forming material of the projection 13 may be the same or different. When the microneedle 11 includes the plurality of projections 13, the forming material of the plurality of projections 13 may be the same or different from each other.

A method for manufacturing the microneedle 11 may be one of a variety of known methods. When the forming material of the microneedle 11 is a resin, a method for manufacturing the microneedle 11 is one of an injection molding method, extrusion molding method, imprint method, hot embossing method, casting method and the like.

When the forming material of the microneedle 11 is silicon or metal, a method for manufacturing the microneedle 11 may be one of a machining method such as cutting, etching method and the like.

Regardless of whether the forming material of the microneedle 11 is any of the above materials, a method for manufacturing the microneedle 11 may be a reproducing method using an intaglio plate as an original plate of the microneedle 11. The intaglio plate is manufactured by, for example, a plating method or a molding method using a resin.

The forming material of the container 21 allows for the deformation of the container 21 when the bottom 22 receives a force in the direction toward the opening 23b. For example, the forming material of the container 21 is a resin such as polyethylene, polypropylene, polyethylene terephthalate or the like. For the container 21 which elastically deforms, a resin film used is preferably made of any of the above materials, and has a thickness in the range from 400 µm to 1000 µm, inclusive. On the other hand, for the container 21 which plastically deforms, a resin film used is preferably made of any of the above materials, and has a thickness in the range from 100 µm to 4000 µm, inclusive.

Furthermore, in the container 21, the amount of force necessary for deformation of the container 21, the direction of force or the way the container 21 deforms varies depending on the shape of the container 21.

Figure 3:
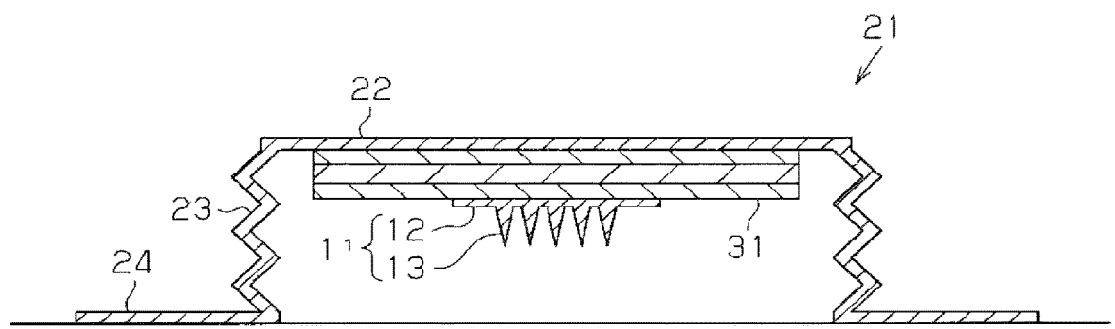
FIG. 3 is a cross sectional view which shows a cross sectional configuration of the microneedle unit in the first embodiment.

For example, as shown in FIG. 3, when the cylindrical body 23 of the container 21 has a plurality of stepped portions arranged in the extending direction of the cylindrical body 23, a force necessary for bringing the bottom 22 of the container 21 close to the opening 23b is small compared with the cylindrical body 23 which does not include stepped portions.

Figure 4:
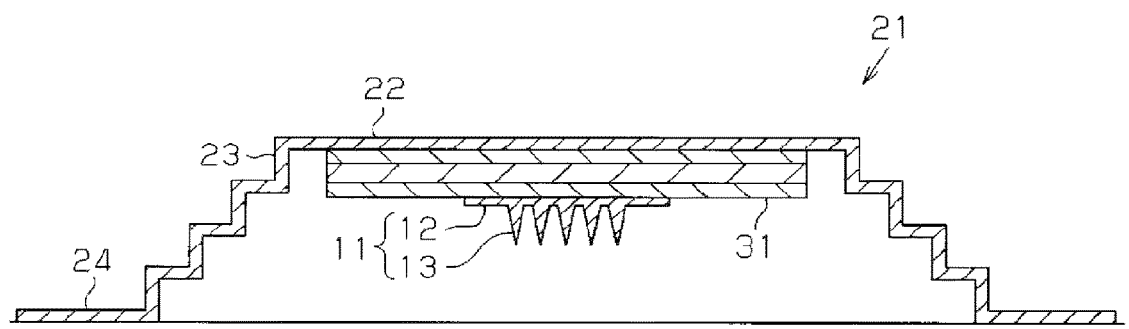
FIG. 4 is a cross sectional view which shows a cross sectional configuration of the microneedle unit in the first embodiment.

For example, as shown in FIG. 4, the cylindrical body 23 of the container 21 may have a plurality of stepped portions arranged in a width direction, which is a direction perpendicular to the extending direction of the cylindrical body 23, with the width of the cylindrical body 23 decreasing from the opening 23b to the bottom 22. In such a cylindrical body 23, when the force that brings the bottom 22 of the container 21 close to the opening 23b is released, the bottom 22 of the container 21 easily moves in a direction away from the opening 23b compared with the cylindrical body 23 which does not include stepped portions.

The forming material of the adhering section 31 is polyurethane material, acrylic material, polyvinyl chloride material, polyvinylidene chloride material, vinyl acetate material, silicone material or the like.

In the adhering section 31, the adhesive strength of the container contact surface 31a to the container 21 is smaller than the adhesive strength of a portion of the target contact surface 31b located in the area surrounding the support surface 12b to the puncture target.

In the adhering section 31 formed of a single layer, the bottom adhesive strength is smaller than the target adhesive strength due to the use of, for example, at least one of the following configuration.

(A) An uneven area is formed, for example, by providing an embossed pattern on the inner surface of the container 21 that is in contact with the container contact surface 31a so as to decrease the contact area between the container 21 and the adhering section 31 to be smaller than the contact area between the puncture target and the adhering section 31.

(B) The inner surface of the container 21 which is in contact with the container contact surface 31a is coated with, for example, silicone material or a fluoride material.

When the adhering section 31 is made up of a plurality of portions, for example, the container contact section 32, the target contact section 33 and the support section 34, the following configuration is used in addition to the above (A) and (B). This contributes to decreasing the adhesive strength of the container contact section 32 to the container 21 to be smaller than the adhesive strength of a portion of the target contact section 33 located in the area surrounding the support surface 12b to the puncture target.

(C) Materials having different adhesive strengths are selected as the forming material of the container contact section 32 and the forming material of the target contact section 33. Particularly, it is preferable that the forming material of the container contact section 32 has an adhesive strength smaller than that of the forming material of the target contact section 33. For example, the forming material of the container contact section 32 may be an adhesive having easy-peel properties, in other words, easy-separation properties, or an adhesive having re-adhesion properties.

(D) The container contact section 32 is formed to be smaller than the support section 34 and the target contact section 33 so that the container contact section 32 is in contact with only part of the support section 34. This contributes to decreasing the contact area between the container 21 and the container contact section 32.

In order to achieve the above (C), an adhesive of easy-separation grade (easy-peel type) such as easy-separation silicone adhesive may be selected from the above adhesive materials as the forming material of the container contact section 32. In this case, the forming material of the target contact section 33 may be any of the above forming materials of the adhering section 31.

In addition, one or more of the above (A) to (D) can be used in combination.

Further, it is preferable that the forming material of the support section 34 has rigidity higher than the forming material of the target contact section 33. The support section 34 is, for example, a resin film made of a resin such as polyethylene, polypropylene and polyethylene terephthalate.

The microneedle unit 10 may include a liquid drug administered into the skin or a liquid drug dissolved in a predetermined solvent. In this case, the microneedle unit 10 may include a drug housing space which is different from the housing space 23a of the microneedle 11 so that the drug is held in the drug housing space. The drug housing space may have any configuration as long as it allows the drug to be supplied to the puncture target when the projection 13 of the microneedle 11 is pierced into the puncture target. Alternatively, if the microneedle unit 10 includes the sealing section 41 and the microneedle 11 is made of a material which is not degraded by a drug, the drug may be held in the housing space 23a of the microneedle 11. In this case, the microneedle unit 10 is preferably configured to have the sealing section 41 when in use.

The drug administered into the skin is pharmacologically active agents, cosmetic composition or the like. When the drug is pharmacologically active agents, the drug is appropriately selected depending on the user's application. When the drug is a pharmacologically active agent, the drug is, for example, vaccines such as influenza vaccine, pain relievers for cancer patients, insulin, biologics, gene therapy agents, injections, oral agents skin application preparations or the like.

Since the microneedle unit 10 is pierced into the skin, percutaneous administration using the microneedle unit 10 is also applied to pharmacologically active agents that need to be subcutaneously injected in addition to the pharmacologically active agents which are conventionally used for percutaneous administration. Particularly, when an injection agent such as vaccine is administered, percutaneous administration using the microneedle unit 10 does not cause pain during drug administration. Accordingly, percutaneous administration using the microneedle unit 10 is preferably applied to children. Further, in percutaneous administration using the microneedle unit 10, a patient does not need to take the drug orally during drug administration to the patient. Accordingly, the microneedle unit 10 is preferably applied to children who have difficulty in taking oral medication.

Cosmetic composition is a composition for use as cosmetics and beauty products. When the drug is a cosmetic composition, the drug is, for example, humectants, colorants, fragrance, physiologically active agents exhibiting cosmetic effects. Active agents exhibiting cosmetic effects are, for example, substances having an improvement effect on wrinkles, acne, stretch marks and the like, or substances having improvement on hair loss.

The container 21 may hold injection liquid inside the container 21 used for administration of the drug into the skin separately from the drug. The injection liquid may be, for example, a water-based solvent such as water or ethylalcohol. The injection liquid may be disposed in the container 21 while being contained in a gel material or a porous material such as a sponge.

Further, the forming material of the projection 13 is a material that is dissolved in the injection liquid held in the container 21, or the forming material of the projection 13 may contain the above drug. In this case, it is preferable that the microneedle unit 10 is configured such that the projection 13 is not in contact with the injection liquid in the container 21 before use of the microneedle unit 10 and the projection 13 is in contact with the injection liquid in use of the microneedle unit 10.

When the container 21 holds the above liquid drug or injection liquid, the container 21 preferably has a through hole through which those liquid is introduced from the outside into the inside of the container 21. After the liquid is introduced into the container 21, the through hole of the container 21 may be closed by a closing member that is disposed inside the through hole and closes the through hole. When the closing member has, for example, a cylindrical shape having two cylindrical ends, it is preferable that a portion of the closing member which is in contact with the outer surface of the container 21 is positioned such that the end on the outer surface of the container 21 has an area larger than the area surrounded by the through hole.

Operation of Microneedle Unit

With reference to FIGS. 5 to 8, an operation of the microneedle unit 10 when a user pierces the microneedle 11 into the puncture target will be described. The puncture target may be, for example, a skin of humans or a skin of animals other than humans. The following describes the operation by means of a configuration example in which the container 21 which can elastically deform includes the flange section 24, the microneedle unit 10 includes the sealing section 41, and the bottom adhesive strength is smaller than the target adhesive strength.

Figure 5:
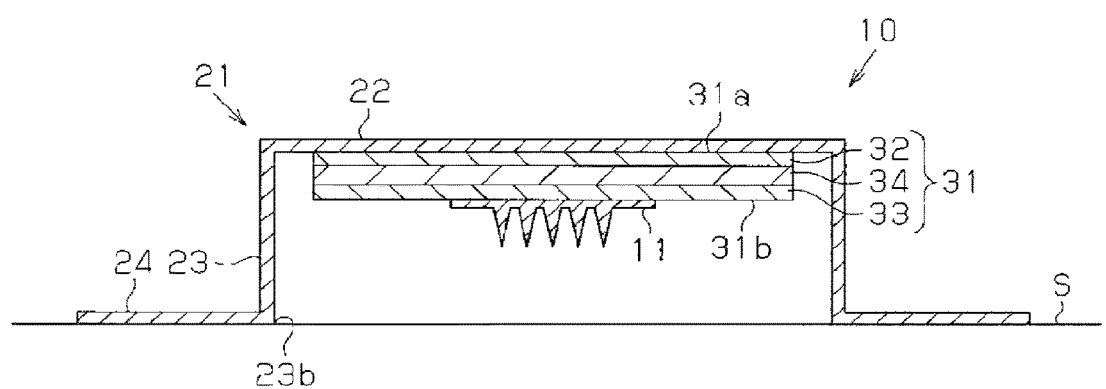
FIG. 5 is an operation view which shows an operation of the microneedle unit in the first embodiment.

As shown in FIG. 5, when a user uses the microneedle unit 10, the user releases adhesive connection between the sealing section 41 and the container 21 so as to remove the sealing section 41 from the microneedle unit 10. The user places the edge of the opening 23b of the container 21 on a skin S of the puncture target. The flange section 24 of the container 21 is positioned on the surface of the skin S. Since the microneedle 11 is surrounded by the container 21 until the microneedle unit 10 is placed on the surface of the skin 5, the microneedle 11 is less likely to be touched by the user. Particularly, in a configuration in which the distal ends of the projections 13 are located in the housing space 23a, the distal ends of the projections 13 are less likely to be touched by the user. Accordingly, the user can handle the microneedle unit 10 with ease when piercing the microneedle 11 into the puncture target.

Figure 6:
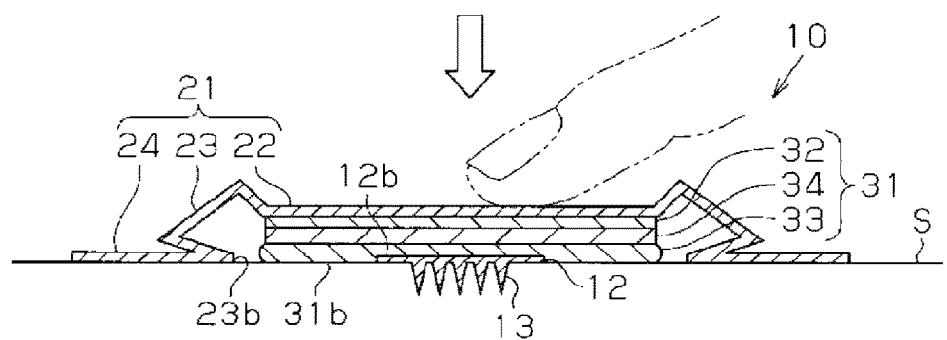
FIG. 6 is an operation view which shows an operation of the microneedle unit in the first embodiment.

As shown in FIG. 6, the user pushes the bottom 22 of the container 21 toward the opening 23b so as to pierce the projections 13 of the microneedle 11 into the skin S of the puncture target. Accordingly, holes are formed in the skin S of the puncture target by the projections 13. In so doing, the container 21 deforms when receiving a force in the direction from the bottom 22 to the opening 23b, thereby allowing the peripheral surface of the cylindrical body 23 to collapse and protrude from the edge of the opening 23b of the cylindrical body 23 to the outside of the opening 23b. As the container 21 exhibits the first deformation, the amount of the portion of the projections 13 which protrude to the outside of the housing space 23a increases. Since the target contact section 33 of the adhering section 31 has rigidity to an extent that can be expanded by a force applied by a user, the target contact section 33 is expanded from the support surface 12b of the base body 12 to the area surrounding the support surface 12b. Then, the target contact section 33 is closely contact with the peripheral surface of the base body 12 and the surface of the skin S.

Figure 7:
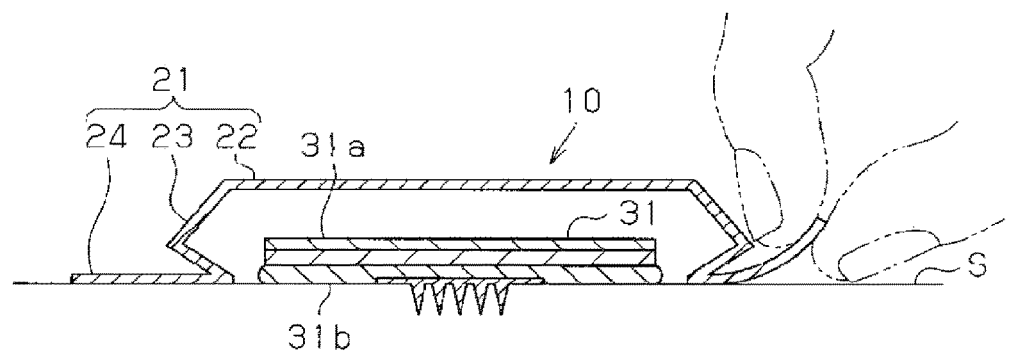
FIG. 7 is an operation view which shows an operation of the microneedle unit in the first embodiment.

As shown in FIG. 7, in elastic deformation of the container 21, as the external force in the direction from the bottom 22 to the opening 23b is released from the bottom 22 by the user, the container 21 allows the distance between the bottom 22 and the opening 23b to increase. As this distance increases, the portion of the peripheral surface of the cylindrical body 23 which protrude from the edge of the opening 23b to the outside of the opening 23b decreases. While the distance between the bottom 22 of the container 21 and the opening 23b increases, the container contact section 32 is adhered to the container 21 and a portion of the target contact section 33 is adhered to the skin S in the adhering section 31. Here, the bottom adhesive strength is smaller than the target adhesive strength. Accordingly, when the distance between the bottom 22 of the container 21 and the opening 23b becomes larger than the length of the adhering section 31 in the extending direction, the container 21 is peeled from the microneedle 11 since the container contact section 32 is peeled from the container 21.

In elastic deformation of the container 21, as the user releases the external force applied to the bottom 22 of the container 21, the container 21 returns to the original shape, thereby allowing the container contact section 32 to be peeled from the bottom 22 of the container 21. Accordingly, the user does not have to perform an additional operation to peel the container 21 from the container contact section 32, that is, an operation to peel the container 21 from the microneedle 11 when he/she stops piecing the microneedle 11 into the skin S.

The user removes the container 21 from the skin S. Since the container 21 has been separated from the container contact section 32, the user can remove the container 21 from the skin S while the microneedle 11 is pierced in the skin S without need of applying a force for separating the container 21 from the container contact section 32. Further, since the flange section 24 of the container 21 is positioned around the surface of the skin S, the user can remove the container 21 from the skin S by holding the flange section 24. Accordingly, the user can easily remove the container 21 compared with the configuration which does not include the flange section 24 in the container 21.

Figure 8:
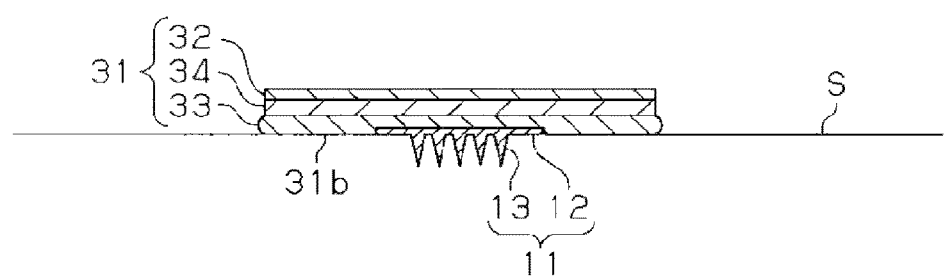
FIG. 8 is an operation view which shows an operation of the microneedle unit in the first embodiment.

As shown in FIG. 8, in the microneedle unit 10, only the microneedle 11 and the adhering section 31 that covers the microneedle 11 are located on the surface of the skin S. In the case of the container 21 that plastically deforms, the container 21 substantially remains in the shape of the container 21 shown in FIG. 6 after the user releases a force applied to the container 21. In this case, the user can also pick the flange section 24 to lift the container 21 from the surface of the skin S so that the force in the direction separating from the puncture target is applied to the bottom 22 to remove the container 21 from the container contact section 32. As a result, in the microneedle unit 10, only the microneedle 11 and the adhering section 31 are located on the surface of the skin S.

The microneedle 11 is housed in the container 21 during a period from when the container 21 is placed on the skin S of the puncture target until when the container 21 is peeled from the microneedle 11. Accordingly, the microneedle 11 is less likely to be touched by the user. Therefore, the user can handle the microneedle unit 10 with ease when piercing the microneedle 11 into the puncture target. Further, if the length of the container 21 in the extending direction is smaller than the length of the projection 13 in the extending direction, the user can pierce the projection 13 into the puncture target while at least part of the projection 13 is housed in the container 21. Accordingly, the user can handle the microneedle unit with ease compared with the configuration in which the user pierces the microneedle into the puncture target while the container is peeled off.

As described above, when the projections 13 of the microneedle 11 is pierced into the skin S, the adhering section 31 that covers the microneedle 11 is located on the surface of the skin S along with the microneedle 11. Accordingly, in the case where the microneedle 11 is applied to the skin S for a long period of time, for example, in the case where the forming material of the microneedle 11 is a drug, or the microneedle 11 dissolves in a drug, it is possible to prevent the microneedle 11 from being peeled off without need for the user to press the microneedle 11 against the skin S.

Moreover, in the case where the microneedle 11 is used to create a hole, the user only has to pick the adhering section 31 when he/she removes the microneedle 11 from the skin S. Accordingly, the hole created in the skin S is less likely to be touched by the user.

Example

Method for Manufacturing Microneedle

In manufacturing of the microneedle 11, an original plate of the microneedle 11 was fabricated by micromachining of a silicon substrate. The silicon substrate was provided with 36 projections, each formed in a regular quadrangular pyramid shape with a height H of 150 μm and a base side length of 60 μm. The respective 36 projections are disposed with an interval of 1 mm in a matrix of 6 columns and 6 lines.

Then, the original plate of the microneedle 11 formed of a silicon substrate was plated with a nickel film with a thickness of 500 μm. After the nickel film was formed, the original plate was etched by wet etching by using 30 wt % potassium hydroxide aqueous solution heated to 90° C. to form an intaglio plate made of nickel.

After the intaglio plate was fabricated, hydroxypropyl cellulose in the liquid form was supplied to the intaglio plate. Then, hydroxypropyl cellulose was cured by heat from a heat source. The cured hydroxypropyl cellulose was peeled off from the intaglio plate to obtain the microneedle 11.

Method for Manufacturing Microneedle Unit

As the container 21 of the microneedle unit 10, a container made of polyethylene terephthalate (PET) was used. The container has a quadrangular cylindrical shape with one of the cylindrical ends being closed. The adhering section 31 was provided as the adhering section 31 which includes the container contact section 32, the target contact section 33, and the support section 34 which is interposed between the container contact section 32 and the target contact section 33. The container contact section 32 was formed of an easy-peel silicone adhesive, the target contact section 33 was formed of an acrylic adhesive, and the support section 34 was formed of polyethylene.

Then, the adhering section 31 was formed by stacking the container contact section 32, the support section 34 and the target contact section 33, and the adhering section 31 was adhered on the inner surface of the container 21 with the microneedle 11 being positioned at the center of the target contact section 33.

Test Method and Test Result

The container 21 of the microneedle unit 10 was pressed against a swine skin while the container 21 was adhered to the microneedle 11 to pierce the projection 13 of the microneedle 11 into the swine skin. Then, the container 21 was released from the swine skin and removed from the swine skin. After the container 21 was removed, the microneedle 11 and the adhering section 31 that covers the microneedle 11 were found to remain on the swine skin.

As described above, according to the microneedle unit 10 of the first embodiments, the following effect can be achieved.

(1) When the projections 13 are pierced into the puncture target, the container 21 that houses the microneedle 11 still surrounds at least part of the projections 13. Then, when the bottom 22 is pushed toward the opening 23b, piercing using the projections 13 continues. After the projections 13 are pierced into the puncture target, the microneedle 11 is peeled from the container 21. Accordingly, when the microneedle 11 is pierced into the puncture target, the microneedle 11 is less likely to be touched by the user. Therefore, the user can handle the microneedle unit 10 with ease when piercing the microneedle 11 into the puncture target.

(2) Since the adhesive strength of the container contact surface 31a to the container 21 is smaller than the adhesive strength of the target contact surface 31b to the puncture target, the container 21 is easily peeled from the microneedle 11.

(3) When the adhering section 31 includes the container contact section 32 and the target contact section 33, the two contact surfaces are made of different forming materials. Accordingly, the degree of freedom of the forming material of the adhering section 31 is improved compared with the case in which two contact surfaces are made of the same material.

(4) The support section 34 having rigidity higher than the target contact section 33 that is in contact with the microneedle 11 supports the target contact section 33. Accordingly, when the container 21 is peeled from the microneedle 11, a force that deforms the target contact section 33 is less likely to be applied to the target contact section 33 since the adhering section 31 includes the support section 34. As a result, the microneedle 11 and thus the projections 13 of the microneedle 11 are resistant to deformation, and the microneedle 11 pierced in the puncture target is prevented from being easily dropped off from the puncture target.

(5) When the microneedle unit 10 is pushed against the puncture target, the flange section 24 is positioned on the surface of the puncture target. Accordingly, when the container 21 is removed from the puncture target, the user can hold the flange section 24 of the container 21, thereby facilitating removal of the container 21.

(6) After the container 21 is pushed against the puncture target to pierce the projection 13 into the skin S, the container 21 is released from the puncture target to allow the container 21 to be peeled from the microneedle 11. Accordingly, the user does not have to perform an additional operation to peel the container 21 from the microneedle 11 when he/she stops piecing the microneedle 11 into the skin S.

Second Embodiment

Figure 9:
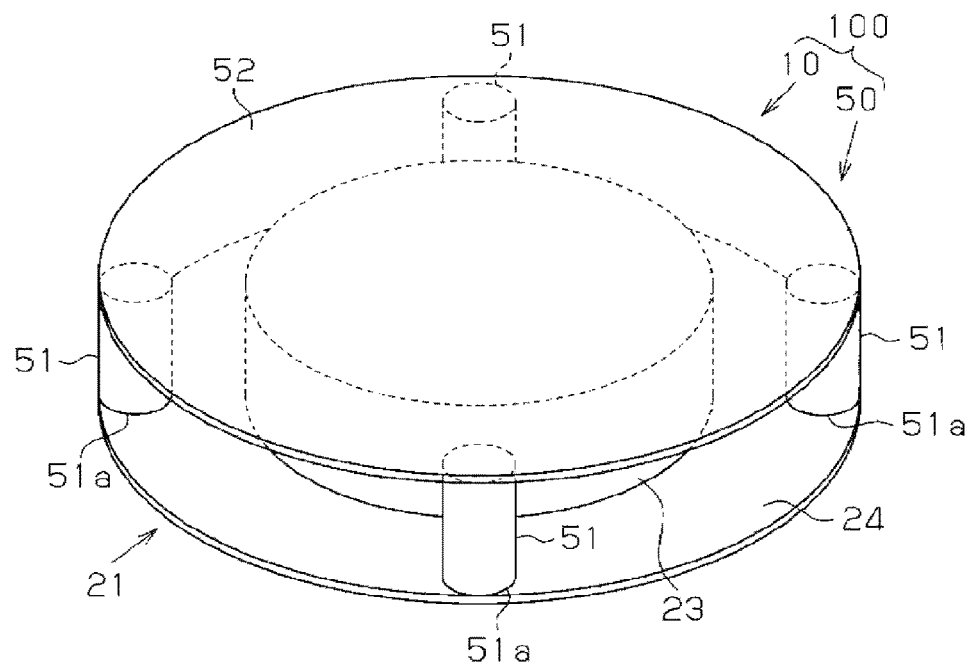
FIG. 9 is a perspective view which shows a perspective configuration of a microneedle assembly in a second embodiment of the microneedle assembly of the present disclosure.

With reference to FIG. 9, the second embodiment of the microneedle assembly according to the technique of the present disclosure will be described. A microneedle assembly of the second embodiment further includes an applicator used for piercing the projections 13 of the microneedle 11 into the puncture target as well as the microneedle unit 10 described in the first embodiment. The following description specifically describes the applicator and the detailed description of the microneedle unit 10 is omitted. Further, in FIG. 9, components similar to those of the microneedle unit 10 of the first embodiment are denoted by the same reference signs.

As shown in FIG. 9, the microneedle assembly 100 includes the microneedle unit 10 and an applicator 50. Similarly to an example of the microneedle unit 10 of the first embodiment, the microneedle unit 10 includes a base body, a microneedle having at least one projection, and a container 21 having a cylindrical body 23 and a flange section 24.

In the microneedle assembly 100, when the microneedle 11 is pierced into the puncture target while the applicator 50 is in contact with the flange section 24 of the microneedle unit 10, the most important thing is to secure the position of the microneedle unit 10 relative to the puncture target.

As shown in FIG. 9, the applicator 50 includes, for example, a plurality of fixing sections 51 and a support section 52 that supports the fixing sections 51. The applicator 50 may include two or more fixing sections 51, and as shown in FIG. 9, the applicator 50 may include four fixing sections 51. The plurality of fixing sections 51 may be disposed on the support section 52 at positions that surround the cylindrical body 23 of the microneedle unit 10. The plurality of fixing sections 51 may be positioned at regular or irregular intervals.

The fixing sections 51 may have a length in the extending direction that reaches the support section 52 and the flange section 24, and may have a columnar shape, spherical shape or elliptical shape. When the fixing section 51 has a columnar shape, each fixing section 51 may be hollow or solid. When the fixing section 51 has a columnar shape, each fixing section 51 may be a round columnar shape or a polygonal columnar shape.

The fixing sections 51 may have elasticity that allows the fixing sections 51 to decrease in length in the extending direction or may have flexibility that allows the fixing sections 51 to flex toward the outside of the support section 52 by a pushing force applied by the user when he/she pushes the support section 52 against the microneedle unit 10. When the fixing sections 51 have flexibility, it is preferable that a fixing surface 51a of each fixing section 51 which is in contact with the flange section 24 has adhesiveness that allows the fixing surface 51a to remain on the flange section 24 if the fixing section 51 flexes.

Alternatively, the fixing section 51 may have rigidity that allows the fixing sections 51 to remain in the original shape when the user pushes the support section 52 against the microneedle unit 10. For the fixing sections 51 that secure the position of the microneedle unit 10 relative to the puncture target, it is preferable that the fixing section 51 has rigidity as described above since the flange section 24 is pressed against the puncture target.

In the fixing section 51, the fixing surface 51a may have adhesiveness that allows for adhesion to the flange section 24 and removal from the flange section 24.

In the fixing section 51, it is preferable that an area of the fixing surface 51a is not larger than an area of a surface of the flange section 24 which faces the fixing section 51. That is, it is preferable that the fixing surfaces 51a are disposed so as not to outwardly extend from the outer edge of the flange section 24. In other words, it is preferable that the entire fixing surfaces 51a overlap the flange section 24 as seen in the pressing direction. Accordingly, the surface of the puncture target is less likely to be contaminated by the applicator 50, since the fixing surfaces 51a of the applicator 50 are not directly in contact with the skin of the puncture target when the applicator 50 fixes the microneedle unit 10 to the puncture target. Therefore, the user can repeatedly use the applicator 50 without sterilizing the applicator 50.

The support section 52 preferably has a plate shape, or may have an annular shape as long as it can support the fixing sections 51. When the support section 52 has a plate shape, as shown in FIG. 9, the support section 52 may have a disc shape or may have a rectangular plate shape. When the support section 52 has an annular shape, it may be an annular shape having ends or an endless annular shape. The support section 52 has flexibility that allows the container 21 to exhibit the first deformation when the user pushes the support section 52 against the microneedle unit 10. When the container 21 of the microneedle unit 10 elastically deforms, it is preferable that the support section 52 of the applicator 50 also elastically deforms.

According to the above applicator 50, the projections of the microneedle can be easily pierced into a position desired by a user, since the projections of the microneedle are pierced into the puncture target while the position of the flange section 24 is fixed to the puncture target by the plurality of fixing sections 51.

When the microneedle unit 10 is applied to the puncture target, the user places the microneedle unit 10 on the skin of the puncture target. Then, while the fixing sections 51 of the applicator 50 is placed on the flange section 24, the user pushes the support section 52 against the microneedle unit 10. Accordingly, the projections of the microneedle are pierced into the puncture target.

When the fixing surface 51a of the fixing section 51 has the above adhesiveness, the fixing surface 51a of the applicator 50 may be first adhered to the flange section 24 of the microneedle unit 10. Then, while the applicator 50 is adhered to the microneedle unit 10, the microneedle unit 10 may be placed on the skin of the user.

As described above, according to the microneedle assembly of the second embodiment, the following effect can be achieved in addition to the above effect of the first embodiment.

(7) The position of the microneedle 11 relative to the puncture target is fixed by the flange section 24 of the container 21 and the applicator 50. Accordingly, the projection of the microneedle can be easily pierced into a position in the puncture target as desired by a user.

The second embodiment described above may be appropriately modified as below.

Figure 10:
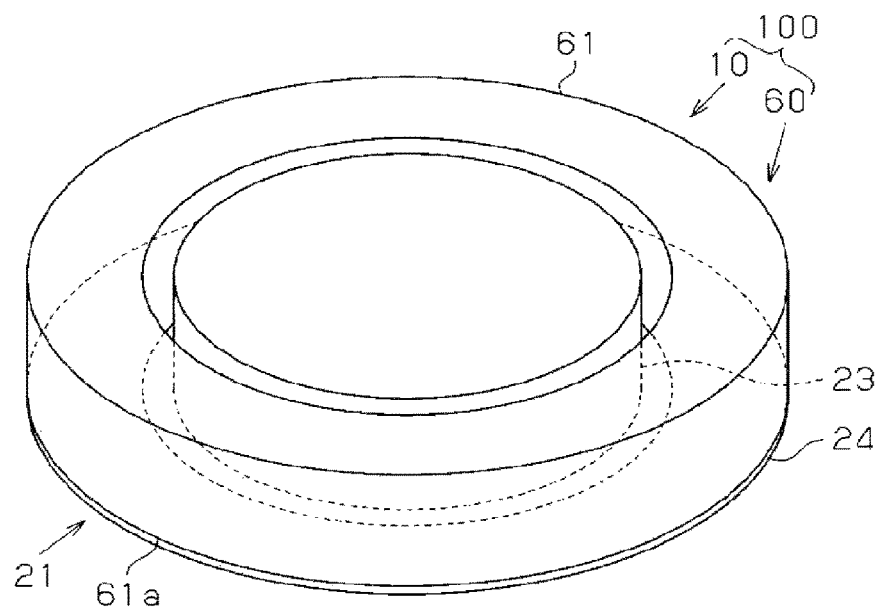
FIG. 10 is a perspective view which shows a perspective configuration of the microneedle assembly in a modified example of the microneedle assembly of the present disclosure.

As shown in FIG. 10, an applicator 60 may have a cylindrical shape that surrounds the periphery of the microneedle unit 10, and may be a fixing section 61 that is in contact with the flange section 24 on a fixing surface 61a which is one of two cylindrical ends. The fixing section 61 may have a round cylindrical shape, a polygonal cylindrical shape or a cylindrical shape having ends. For the fixing section 61 that surrounds the periphery of the microneedle 11, it is preferable that the fixing section 61 has the same shape as the cylindrical body 23 of the microneedle 11. When the cylindrical body 23 has a cylindrical shape, the fixing section 61 preferably has a cylindrical shape.

The fixing section 61 may have a fixing surface 61a which has adhesiveness to the flange section 24 of the microneedle 11. The adhesiveness of the fixing surface 61a is preferably to the extent that allows the fixing surface 61a to be easily adhered to the flange section 24 and easily separated from the flange section 24. In the fixing section 61, a fitting section that fits with the flange section 24 may be disposed on the fixing surface 61a. Since the fixing surface 61a of the fixing section 61 is provided with adhesiveness or the fitting section is positioned on the fixing surface 61a, the position of the microneedle unit 10 relative to the fixing section 61 is less likely displaced.

In the fixing section 61, it is preferable that an area of the fixing surface 61a is not larger than an area of a surface of the flange section 24 which faces the fixing section 61. That is, it is preferable that the outer edge of the fixing surface 61a is located on the outer edge of the flange section 24 or the outer edge of the fixing surface 61a is located inside the outer edge of the flange section 24.

Third Embodiment

With reference to FIGS. 11 to 14, a third embodiment of the microneedle assembly according to the technique of the present disclosure will be described. The microneedle assembly of the third embodiment differs from the microneedle assembly of the second embodiment in the configuration of the applicator. Accordingly, the following description specifically describes the difference and the detailed description of the remaining configuration is omitted.

Figure 11:
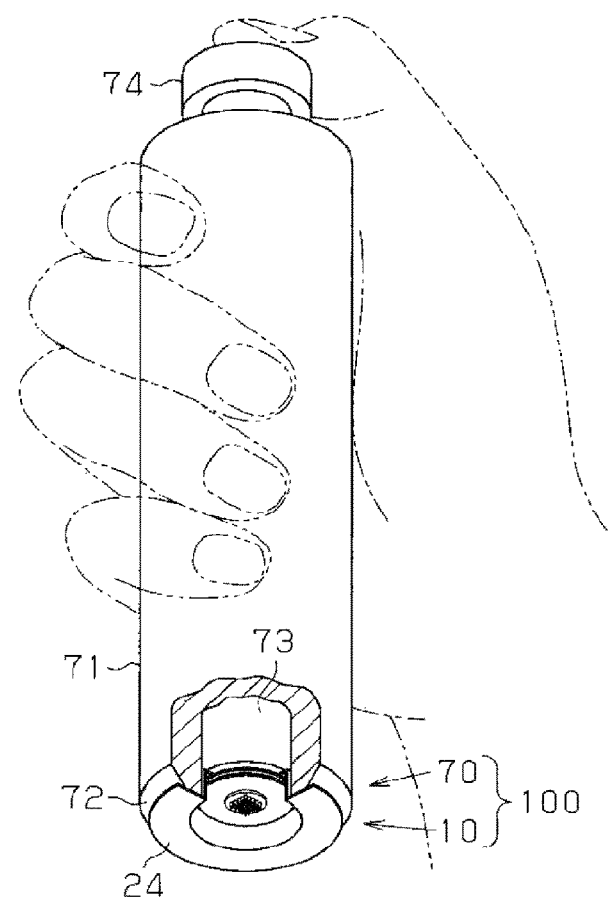
FIG. 11 is a perspective view which shows a perspective configuration of a microneedle in a third embodiment of the microneedle assembly of the present disclosure.

As shown in FIG. 11, it is most important for an applicator 70 to have a pushing mechanism 73 that pushes the container 21 of the microneedle unit 10 against the puncture target. The pushing mechanism 73 is one example of the pushing section.

The applicator 70 includes a main body 71 having a cylindrical shape, and the main body 71 has two cylindrical ends, one of which is a proximal end and the other is a distal end. The main body 71 includes a fixing section 72 on the distal end. The fixing section 72 may have a decreased diameter compared with the other portions of the main body 71. A fixing surface 72a of the fixing section 72 preferably has adhesiveness that allows for adhesion to the flange section 24 of the microneedle unit 10 and removal from the flange section 24.

In the fixing section 72, it is preferable that an area of the fixing surface 72a is not larger than an area of a surface of the flange section 24 which faces the fixing section 72. That is, it is preferable that the outer edge of the fixing surface 72a is located on the outer edge of the flange section 24 or the outer edge of the fixing surface 72a is located inside the outer edge of the flange section 24.

The pushing mechanism 73 is disposed in the main body 71, and extends from the proximal end of the main body 71 and is located at a position close to the proximal end than to the distal end of the main body 71. The pushing mechanism 73 has a cylindrical shape which is spaced from the inner periphery of the main body 71 at least on the distal end of the main body 71. The proximal end of the pushing mechanism 73 is exposed through the proximal end of the main body 71. An operation section 74 is disposed on the distal end of the pushing mechanism 73 so as to move the distal end of the pushing mechanism 73 to the distal end of the main body 71.

When a force is applied to the operation section 74 to push the operation section 74 toward the distal end of the main body 71, at least the distal end of the pushing mechanism 73 moves to the distal end of the main body 71. When the fixing section 72 is located on the flange section 24 of the microneedle unit 10, the pushing mechanism 73 moves toward the distal end of the main body 71, thereby pushing the container 21 against the puncture target with a predetermined amount of force. When a force applied to the operation section 74 is released, at least the distal end of the pushing mechanism 73 moves to the proximal end of the main body 71 to a position close to the proximal end by a predetermined amount of distance. When a force applied to the operation section 74 is released, the distal end of the pushing mechanism 73 may be or may not be in contact with the container 21.

When the user uses the applicator 70, the user grips the main body 71 of the applicator 70 and puts one finger, for example, a thumb, on the operation section 74.

Figure 12:
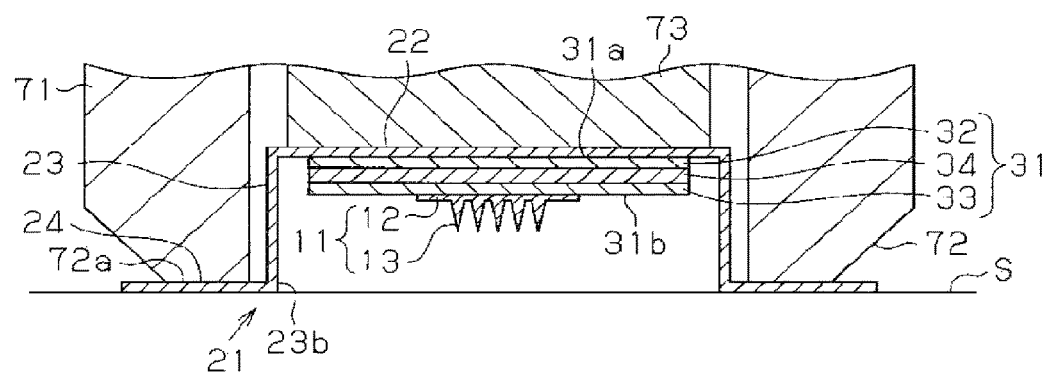
FIG. 12 is a cross sectional view which shows a cross sectional configuration of the microneedle assembly in the third embodiment.

As shown in FIG. 12, the microneedle unit 10 is placed on the skin S of the puncture target and the fixing surface 72a of the applicator 70 is placed on the flange section 24 of the microneedle unit 10. Alternatively, while the fixing surface 72a of the applicator 70 is adhered to the flange section 24 of the microneedle unit 10, the applicator 70 along with the microneedle unit 10 is placed on the skin S of the puncture target.

The distal end of the pushing mechanism 73 is in contact with the bottom 22 of the container 21 and the peripheral surface of the cylindrical body 23 is located spaced from the inner peripheral surface of the main body 71.

Figure 13:
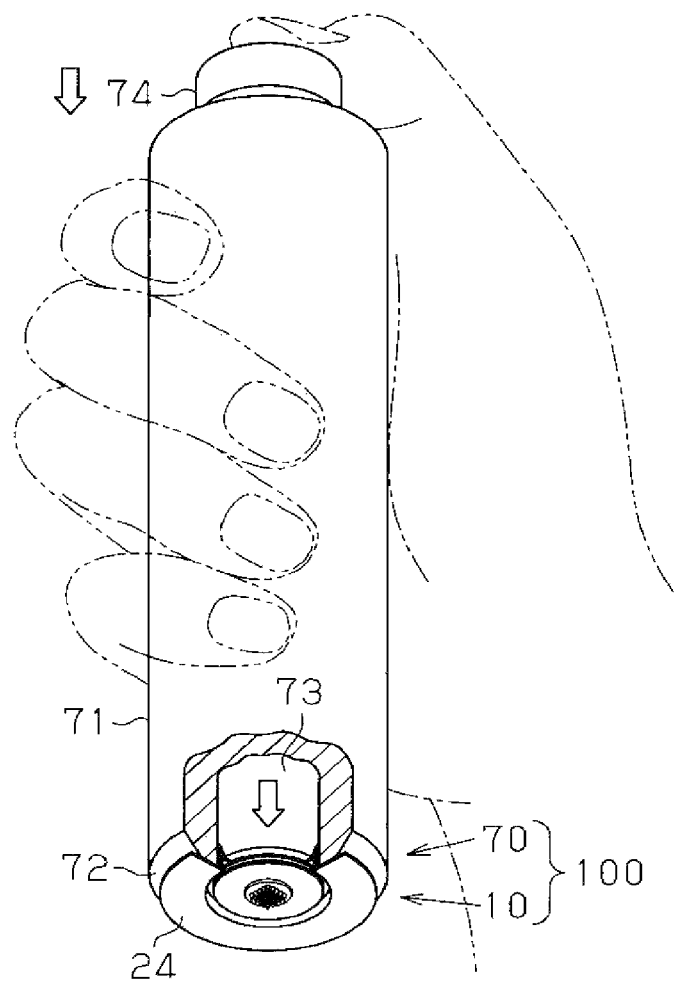
FIG. 13 is a perspective view which shows a perspective configuration of the microneedle assembly in the third embodiment.

As shown in FIG. 13, when the user pushes the operation section 74 with his/her thumb to the distal end of the main body 71, the distal end of the pushing mechanism 73 moves toward the distal end of the main body 71, thereby pushing the bottom 22 of the container 21 of the microneedle unit 10 into the opening 23b.

Figure 14:
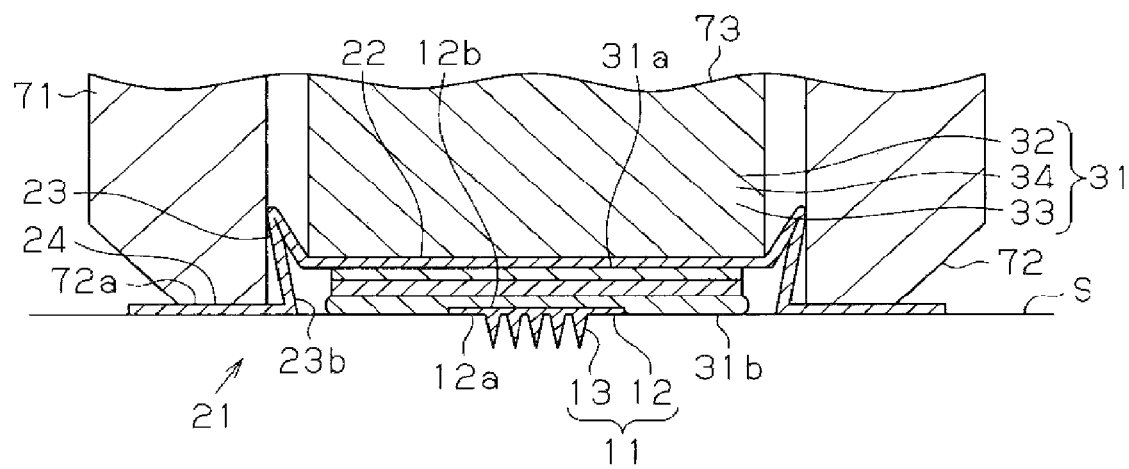
FIG. 14 is a cross sectional view which shows a cross sectional configuration of the microneedle assembly in the third embodiment.

As shown in FIG. 14, the bottom 22 of the container 21 is pushed against the skin S of the puncture target by the distal end of the pushing mechanism 73. Accordingly, as the cylindrical body 23 deforms, part of the cylindrical body 23 is positioned in a space between the main body 71 and the pushing mechanism 73. Further, as the bottom 22 of the container 21 moves to the opening 23b, the projections 13 of the microneedle 11 are pierced into the skin S and the target contact section 33 is expanded from the support surface 12b of the base body 12 to an area surrounding the support surface 12b. Accordingly, the target contact section 33 is in close contact with the peripheral surface of the base body 12 and the surface of the skin S.

When the user removes the applicator 70 from the microneedle unit 10, the microneedle unit 10 remains in the skin S while the projections 13 are pierced into the skin S. When the adhesive strength between the fixing surface 72a of the applicator 70 and the flange section 24 is larger than the adhesive strength between the container 21 and the container contact section 32 and smaller than the adhesive strength between the puncture target and the target contact section 33, the container 21 is removed from the skin S when the user moves the applicator 70 away from the skin S.

According to the applicator 70 described above, since the user can pierce the projections 13 of the microneedle 11 into the skin S of the puncture target by using the pushing mechanism 73, an operation to pierce using the projections 13 of the microneedle 11 can be easily performed. Furthermore, since the projections 13 of the microneedle 11 are pushed against the skin S of the puncture target by the pushing mechanism 73 of the applicator 70, the microneedle 11 is pushed against the skin S of the puncture target with a predetermined amount of force regardless of displacement of the user. Accordingly, variation can be minimized in the extent of piercing the projections 13 of the microneedle 11 into the skin S.

As described above, according to the microneedle assembly 100 of the third embodiment, the following effect can be achieved in addition to the microneedle assembly 100 of the second embodiment.

(8) An operation to pierce the projections 13 of the microneedle 11 into the puncture target can be easily performed.

Further, the above embodiments may also be modified as below.

The adhesive strength of the container contact section 32 to the bottom 22 may be larger than the adhesive strength of the container contact section 32 to the support section 34, and may be larger than the adhesive strength of the target contact section 33 to the support section 34. Further, a peeling adhesive strength, which is a smaller adhesive strength of the adhesive strength of the container contact section 32 to the support section 34 and the adhesive strength of the target contact section 33 to the support section 34, is smaller than the target adhesive strength. In other words, the adhesive strength of the target contact surface 31b to the skin is larger than a force necessary for increasing a distance between the target contact surface 31b and the bottom 22.

Figure 15:
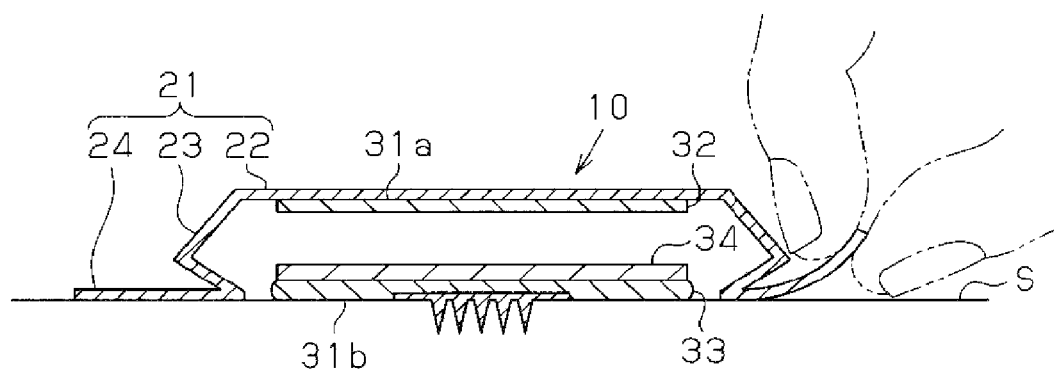
FIG. 15 is an operation view which shows an operation of the microneedle unit in a modified example.

For example, as shown in FIG. 15, the adhesive strength of the container contact section 32 to the support section 34 may be the peeling adhesive strength. In this configuration, when the container 21 exhibits the second deformation, the target contact surface 31b remains adhered to the skin of the puncture target, and adhesion between the container contact section 32 and the support section 34 is released.

Figure 16:
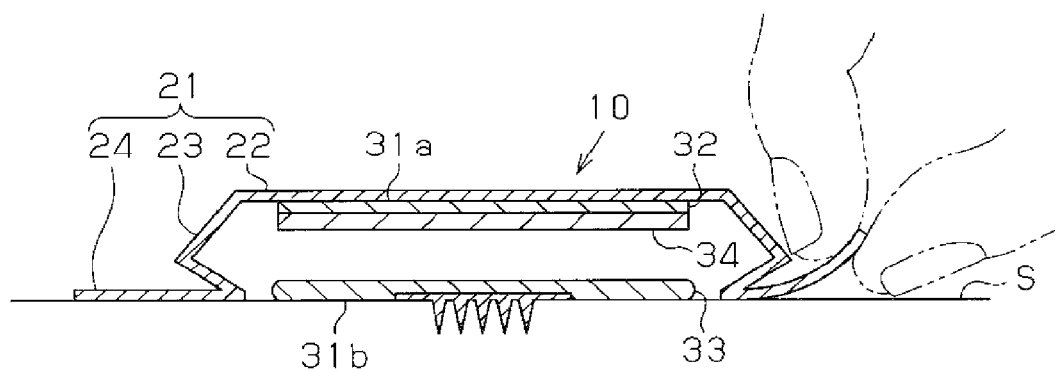
FIG. 16 is an operation view which shows an operation of the microneedle unit in a modified example.

Further, as shown in FIG. 16, the adhesive strength of the target contact section 33 to the support section 34 may be the peeling adhesive strength. In this configuration, when the container 21 exhibits the second deformation, the target contact surface 31b remains adhered to the skin of the puncture target, and adhesion between the target contact section 33 and the support section 34 is released.

The projection of the microneedle is covered by a cover before the microneedle is used by a user, and the cover is adhered to a portion of the microneedle other than the projection by an adhesive. The user removes the cover from the microneedle when using the microneedle.

Since the user needs to remove the cover from the microneedle, the microneedle may be touched by the user's finger or the cover depending on the way the user removes the cover. The projection of the microneedle is formed to have a size that does not provoke pain to the puncture target. Accordingly, there is a risk that the tip of the projection is bent in a direction which is not suitable for piercing into the puncture target if the microneedle is touched by the user's finger or the cover before it is pierced into the puncture target. Thus, handling of the microneedle is difficult for the user when piercing the microneedle into the puncture target. Accordingly, it is desired to provide microneedles configured to protect the projection from being touched by the user's finger or the cover.

The technique of the present disclosure has an object of providing a microneedle unit and a microneedle assembly having improved handling properties in piercing of the microneedle into a puncture target.

In one aspect of the technique of the present disclosure, a microneedle unit includes: a microneedle which includes a facing surface having one or more projections and a support surface which is a surface opposite to the facing surface; a recessed container having an opening and a bottom, the recessed container being provided with a housing space that houses the microneedle so that the facing surface faces an outside of the recessed container through the opening; and an adhering section that adheres to the bottom and the support surface. A direction from the bottom to the opening is a pressing direction, and the recessed container is configured to allow deformation due to an external force in the pressing direction being applied to the bottom. The deformation of the recessed container includes displacement of the bottom in the pressing direction and displaces the projection in the pressing direction on the outside of the housing space. The adhering section includes a first contact surface that is in contact with the bottom, and a second contact surface that is in contact with the support surface and extends from the support surface to an area surrounding the support surface, and the deformation of the recessed container causes the second contact surface in the area surrounding the support surface to be pushed out of the housing space via the opening.

According to one aspect of the microneedle unit of the technique of the present disclosure, when the bottom of the recessed container that houses the microneedle is pushed against the puncture target, the projection is pierced into the puncture target. Accordingly, when the microneedle is pierced into the puncture target, the microneedle is less likely to be touched by the user. As a result, the user can handle the microneedle unit with ease when piercing the microneedle into the puncture target.

In another aspect of the microneedle unit of the technique of the present disclosure, the deformation of the recessed container is a first deformation, and the recessed container is configured to allow a second deformation due to a force in a direction opposite to the pressing direction being applied to the bottom, and the second deformation includes displacement of the bottom in the direction opposite to the pressing direction. The adhering section has adhesiveness that maintains adhesion between a portion of the second contact surface located in the area surrounding the support surface and a skin which is a puncture target while allowing the first contact surface to be peeled from the bottom when the recessed container performs the second deformation.

According to one aspect of the microneedle unit of the technique of the present disclosure, after the projection is pierced into the puncture target, the microneedle is peeled from the recessed container. Accordingly, the user can handle the microneedle with ease when piercing the microneedle into the puncture target.

In another aspect of the microneedle unit of the technique of the present disclosure, it is preferable that an adhesive strength of the second contact surface to the skin is larger than a force necessary for increasing a distance between the second contact surface and the bottom.

According to another aspect of the microneedle unit of the technique of the present disclosure, the recessed container is easily peeled from the microneedle since the adhesive strength of the second contact surface to the skin is larger than a force necessary for increasing a distance between the second contact surface and the bottom.

In another aspect of the microneedle unit of the technique of the present disclosure, a forming material of the first contact surface and a forming material of the second contact surface are different from each other.

According to another aspect of the microneedle unit of the technique of the present disclosure, the degree of freedom of the forming material of the adhering section is improved compared with the case in which two contact surfaces are made of the same material, since two contact surfaces are made of different forming materials.

In another aspect of the microneedle unit of the technique of the present disclosure, the adhering section includes: a first portion having the first contact surface; a second portion having the second contact surface; and a third portion disposed between the first portion and the second portion, the third portion having rigidity higher than the second portion.

According to another aspect of the microneedle unit of the technique of the present disclosure, the adhering section includes the third portion having rigidity higher than the second portion that is in contact with the microneedle. Accordingly, when the recessed container is peeled from the microneedle, a force that deforms the second portion is less likely to be applied to the second portion since the adhering section includes the third portion. As a result, the microneedle and thus the projections of the microneedle are resistant to deformation, and the microneedle pierced in the puncture target is prevented from being easily dropped off from the puncture target.

In another aspect of the microneedle unit of the technique of the present disclosure, the recessed container further includes a flange section that extends from an edge of the opening to the outside of the recessed container.

According to another aspect of the microneedle unit of the technique of the present disclosure, the flange section is positioned on the surface of the puncture target when the microneedle unit is pushed against the puncture target. Accordingly, when the recessed container is removed from the puncture target, the user can hold the flange section of the recessed container. This facilitates removing the recessed container from the puncture target.

In another aspect of the microneedle unit of the technique of the present disclosure, the second deformation is elastic deformation that displaces the bottom in a direction opposite to the pressing direction when the force in the pressing direction is released from the bottom.

According to another aspect of the microneedle unit of the technique of the present disclosure, after the bottom is pushed against the puncture target so that the projection is pierced into the skin, an operation to push the bottom against the puncture target stops, to help the recessed container to be peeled from the microneedle. Accordingly, the user is released from the task of operation to peel the recessed container from the microneedle when he/she stops piecing the microneedle into the skin.

In one aspect of the technique of the present disclosure, a microneedle assembly includes a microneedle unit and an applicator. The microneedle unit includes: a microneedle which includes a facing surface having one or more projections and a support surface which is a surface opposite to the facing surface; a recessed container having a bottom and an opening, the recessed container being provided with a housing space that houses the microneedle so that the facing surface faces an outside of the recessed container through the opening and including a flange section that extends outward from an edge of the opening; and an adhering section that adheres to the bottom and the support surface. A direction from the bottom to the opening is a pressing direction, the recessed container is configured to allow deformation due to an external force in the pressing direction being applied to the bottom, and the deformation of the recessed container includes displacement of the bottom in the pressing direction and displaces the projection in the pressing direction on the outside of the housing space, and the adhering section includes a first contact surface that is in contact with the bottom, and a second contact surface that is in contact with the support surface and extends from the support surface to an area surrounding the support surface, and the deformation of the recessed container causes the second contact surface in the area surrounding the support surface to be pushed out of the housing space via the opening. The applicator has a surface that is in contact with the flange section and pushes the flange section against the puncture target.

In one aspect of the microneedle assembly of the technique of the present disclosure, a position of the microneedle relative to the puncture target is stabilized by the flange section of the recessed container and the applicator. Accordingly, the projection of the microneedle can be easily pierced into a position in the puncture target as desired by a user.

In another aspect of the microneedle assembly of the technique of the present disclosure, it is preferable that the area of the surface of the flange section which faces the applicator is not smaller than the area of the surface of the applicator which is in contact with the flange section.

In another aspect of the microneedle assembly of the technique of the present disclosure, since the applicator is not in contact with the target, the surface of the target is less likely to be contaminated by the applicator.

In another aspect of the microneedle assembly of the technique of the present disclosure, the applicator further includes a pushing section that pushes the bottom of the microneedle unit against the puncture target.

According to another aspect of the microneedle assembly of the technique of the present disclosure, a piercing operation using the projection of the microneedle can be easily performed.

According to the microneedle unit and the microneedle assembly of the technique of the present disclosure, handling during piercing of the microneedle into the target can be easily performed.

REFERENCE SIGNS LIST

10 . . . microneedle unit, 11 . . . microneedle, 12 . . . base body, 12a . . . facing surface, 12b . . . support surface, 13 . . . projection, 21 . . . container, 22 . . . bottom, 23 . . . cylindrical body, 23a . . . housing space, 23b . . . opening, 24 . . . flange section, 31 . . . adhering section, 31a . . . container contact surface, 31b . . . target contact surface, 32 . . . container contact section, 33 . . . target contact section, 34, 52 . . . support section, 41 . . . sealing section, 50, 60, 70 . . . applicator, 51, 61, 72 . . . fixing section, 51a, 61a, 72a . . . fixing surface, 71 . . . main body, 73 . . . pushing mechanism, 74 . . . operation section, 100 . . . microneedle assembly, S . . . skin.

Obviously, numerous modifications and variations of the present invention are possible in light of the above teachings. It is therefore to be understood that within the scope of the appended claims, the invention may be practiced otherwise than as specifically described herein.

What is claimed is:

1. A microneedle unit, comprising:
a microneedle including a facing surface having at least one projection formed thereon and a support surface opposite to the facing surface;
a recessed container having a housing space between an opening and a bottom of the recessed container for housing the microneedle such that the microneedle has the facing surface facing outside of the recessed container through the opening; and
an adhering structure having a first contact surface directly adhered to the bottom of the recessed container and a second contact surface adhered to the support surface of the microneedle such that the second contact surface is extending outside the support surface of the microneedle,
wherein the recessed container has a cylindrical body configured to deform upon receiving an external force applied to the bottom of the recessed container in a pressing direction from the bottom of the recessed container to the opening of the recessed container such that the bottom of the recessed container is displaced in the pressing direction, that the at least one projection of the microneedle is displaced in the pressing direction on an outside of the housing space, and that a portion of the second contact surface of the adhering structure positioned outside the support surface of the microneedle is pushed toward the outside of the housing space of the microneedle, and the recessed container has an inner surface formed to contact with the first contact surface of the adhering structure such that the inner surface is configured to separate from the first contact surface of the adhering structure.

2. The microneedle unit of claim 1, wherein the cylindrical body of the recessed container has a plurality of stepped portions configured to deform upon receiving the external force applied to the bottom and to deform elastically upon releasing the external force from the bottom of the recessed container, and the adhering structure has the second contact surface having adhesiveness sufficient to keep the portion of the second contact surface outside the support surface adhered to a target when the first contact surface of the adhering structure separates from the inner surface of the recessed container.

3. The microneedle unit of claim 2, wherein the adhering structure has the second contact surface having an adhesive strength to a target such that the adhesive strength of the second contact surface is larger than a force that separates the first contact surface of the adhering structure from the inner surface of the recessed container.

4. The microneedle unit of claim 3, wherein the adhering structure comprises a first portion having the first contact surface and a second portion having the second contact surface such that the first portion is fixed to the second portion and that the first portion and the second portion are made of different materials.

5. The microneedle unit of claim 3, wherein the adhering structure includes a first portion having the first contact surface, a second portion having the second contact surface, and a third portion disposed between the first portion and the second portion, the first portion is fixed to the third portion, and the third portion is more rigid than the second portion.

6. The microneedle unit of claim 3, wherein the recessed container further includes a flange portion that extends outward from an edge of the opening.

7. The microneedle unit of claim 2, wherein the adhering structure comprises a first portion having the first contact surface and a second portion having the second contact surface such that the first portion is fixed to the second portion and that the first portion and the second portion are made of different materials.

8. The microneedle unit of claim 2, wherein the adhering structure includes a first portion having the first contact surface, a second portion having the second contact surface, and a third portion disposed between the first portion and the second portion, the first portion is fixed to the third portion, and the third portion is more rigid than the second portion.

9. The microneedle unit of claim 2, wherein the recessed container further includes a flange portion that extends outward from an edge of the opening.

10. The microneedle unit of claim 2, wherein the recessed container is formed such that the inner surface has a coating comprising a silicone material or a fluoride material.

11. The microneedle unit of claim 1, wherein the adhering structure has the second contact surface having an adhesive strength to a target such that the adhesive strength of the second contact surface is larger than a force that separates the first contact surface of the adhering structure from the inner surface of the recessed container.

12. The microneedle unit of claim 1, wherein the adhering structure comprises a first portion having the first contact surface and a second portion having the second contact surface such that the first portion is fixed to the second portion and that the first portion and the second portion are made of different materials.

13. The microneedle unit of claim 1, wherein the adhering structure includes a first portion having the first contact surface, a second portion having the second contact surface, and a third portion disposed between the first portion and the second portion, the first portion is fixed to the third portion, and the third portion is more rigid than the second portion.

14. The microneedle unit of claim 1, wherein the recessed container further includes a flange portion that extends outward from an edge of the opening.

15. The microneedle unit of claim 1, wherein the cylindrical body of the recessed container is configured to deform elastically upon releasing the external force from the bottom of the recessed container such that the bottom of the recessed container is displaced in a direction opposite to the pressing direction, and the recessed container and the adhering structure is formed such that the first contact surface of the adhering structure separates from the inner surface of the recessed container when the portion of the second contact surface adheres to the target and the bottom of the recessed container is displaced in the direction opposite to the pressing direction.

16. The microneedle unit of claim 1, wherein the recessed container is formed such that the inner surface has an embossed pattern.

17. A microneedle assembly, comprising:
a microneedle unit; and
an applicator configured to apply the microneedle unit to a target,
wherein the microneedle unit includes a microneedle having a facing surface having at least one projection formed thereon and a support surface opposite to the facing surface, a recessed container having a housing space between an opening and a bottom of the recessed container for housing the microneedle, and a flange portion extending outward from an edge of the opening such that the microneedle has the facing surface facing outside of the recessed container through the opening, and an adhering structure having a first contact surface directly adhered to the bottom of the recessed container and a second contact surface adhered to the support surface of the microneedle such that the second contact surface is extending outside the support surface, the recessed container has a cylindrical body configured to deform upon receiving an external force applied to the bottom of the recessed container in a pressing direction from the bottom to the opening of the recessed container such that the bottom of the recessed container is displaced in the pressing direction, that the at least one projection is displaced in the pressing direction on an outside of the housing space, and that a portion of the second contact surface of the adhering structure positioned outside the support surface of the microneedle is pushed toward the outside of the housing space, the recessed container has an inner surface formed to contact with the first contact surface of the adhering structure such that the inner surface is configured to separate from the first contact surface of the adhering structure, and the applicator has a fixing body having a fixing surface configured to contact with the flange portion of the microneedle unit when the flange portion is pushed against the target.

18. The microneedle assembly of claim 17, wherein the flange portion of the recessed container has a surface which faces the fixing body of the applicator and has an area not smaller than an area of the fixing surface of the fixing body in contact with the flange portion of the recessed container.

19. The microneedle assembly of claim 18, wherein the applicator further includes a pushing body that pushes the bottom of the microneedle unit against the target.

20. The microneedle assembly of claim 17, wherein the applicator further includes a pushing body that pushes the bottom of the microneedle unit against the target.

* * * * *